United States Patent
Frycek et al.

(10) Patent No.: US 9,908,839 B2
(45) Date of Patent: Mar. 6, 2018

(54) PROCESS FOR PRODUCING LOW VOC COALESCING AIDS

(71) Applicant: Dow Global Technologies LLC, Midland, MI (US)

(72) Inventors: George J. Frycek, Midland, MI (US); Andrei S. Merenov, Lake Jackson, TX (US); Felipe A. Donate, Midland, MI (US); Edward D. Daugs, Midland, MI (US); Julie L. Maurer, Midland, MI (US); Rebecca J. Wachowicz, Bay City, MI (US); Jason L. Trumble, Bay City, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/318,009

(22) PCT Filed: Jun. 18, 2015

(86) PCT No.: PCT/US2015/036388
§ 371 (c)(1),
(2) Date: Dec. 12, 2016

(87) PCT Pub. No.: WO2015/200088
PCT Pub. Date: Dec. 30, 2015

(65) Prior Publication Data
US 2017/0113997 A1   Apr. 27, 2017

Related U.S. Application Data

(60) Provisional application No. 62/016,311, filed on Jun. 24, 2014.

(51) Int. Cl.
*C07C 69/66* (2006.01)
*C07C 67/08* (2006.01)
*C09D 7/12* (2006.01)

(52) U.S. Cl.
CPC ............ *C07C 67/08* (2013.01); *C09D 7/1233* (2013.01)

(58) Field of Classification Search
CPC .............................. C09D 7/1233; C07C 67/08
USPC ......................................................... 560/186
See application file for complete search history.

(56) References Cited

U.S. PATENT DOCUMENTS

| | | | |
|---|---|---|---|
| 3,168,553 A | 2/1965 | Slaugh et al. | |
| 3,507,891 A | 4/1970 | Hearne et al. | |
| 4,022,808 A | 5/1977 | Yoshihara et al. | |
| 4,115,415 A | 9/1978 | Yoshihara et al. | |
| 4,489,188 A | 12/1984 | Jones et al. | |
| 5,618,973 A | 4/1997 | Papa et al. | |
| 6,284,919 B1 | 9/2001 | Pearson et al. | |
| 6,348,621 B1 | 2/2002 | Wang et al. | |
| 6,476,255 B1 | 11/2002 | Hadden et al. | |
| 6,916,950 B2 | 7/2005 | Gubisch et al. | |
| 8,901,343 B2 | 12/2014 | Disteldorf et al. | |
| 8,962,541 B2 | 2/2015 | Godwin et al. | |
| 2011/0184207 A1 | 7/2011 | Wu et al. | |
| 2012/0258249 A1* | 10/2012 | Adamson | C09D 163/00 427/385.5 |
| 2012/0259049 A1* | 10/2012 | Donate | C09D 9/005 524/290 |

FOREIGN PATENT DOCUMENTS

| | | |
|---|---|---|
| DE | 240005 A1 | 10/1986 |
| DE | 240006 A1 | 10/1986 |
| EP | 2508572 A1 * | 10/2012 |
| GB | 2048627 | 12/1980 |
| WO | 99/36385 | 7/1999 |

OTHER PUBLICATIONS

Aranda et al., "Acid-Catalyzed Homogeneous Esterification Reaction for Biodiesel Production from Palm Fatty Acids", Catal. Lett. (2008), 122 p. 20-25.
Brewster et al, Unitized Experiments in Organic Chemistry 3rd Edition, (1970) p. 101-105.
Clegg et al., "Highly active and selective catalysts for the production of methyl propanoate via the methoxycarbonylation of ethene", Chem. Comm., 1999, pp. 1877-1878.
Hidai, "Synthesis of Ketones and Esters from Olefins, Carbon Monoxide and Alcohols by using Ruthenium-iodide catalysts", Journal of Molecular Catalysis, 40 (1987), pp. 243-254.
Ishihara, "Dehydrative condensation catalyses", Tetrahedron 65 (2009), p. 1085-1109.
Baker et al., "tert-Butyl Acetate", Organic Synthesis, Collective vol. 3, p141 (1955); vol. 24 p. 18, (1944).
Research Disclosure, "Catalyst for transesterification of Alkyl 3-Alkoxypropionates", vol. 276, 04 1987, p. 266.
Yusude et al., "Vapor Phase Carbonylation of Organic Halo Compounds", Bull. Chem. Soc. Jpn, 1992, 65, pp. 289-291.
PCT/US2015/036388, International Search Report & Written Opinion dated Sep. 21, 2015.
PCT/US2015/036388, International Preliminary Report on Patentability dated Dec. 27, 2016.

* cited by examiner

*Primary Examiner* — Deborah D Carr

(57) ABSTRACT

A process comprising reacting a mono- or di-carboxylic acid and/or acid anhydride with a glycol ether in the presence of phosphoric acid to produce a glycol ether ester product having low color and low VOC content.

13 Claims, No Drawings

US 9,908,839 B2

PROCESS FOR PRODUCING LOW VOC COALESCING AIDS

BACKGROUND OF THE INVENTION

The invention relates to a process for the preparation of low VOC glycol ether esters.

Coalescing aids are added to waterborne paints (i.e., latex paints) to allow the formation of a continuous polymer or binder film as water evaporates from the system. Without the addition of these coalescing aids, latex polymer spheres are not likely to soften and deform, which is a requirement in film formation. As a result, the polymer cannot act as a binder for the pigments in the paint and no adhesion to the substrate (e.g., interior or exterior wall) can occur. For many years, coalescing aids have been volatile solvents, such as 2,2,4-trimethyl-1,3-pentanediol monoisobutyrate, commercially available from Eastman under the trade name TEXANOL.

Volatile organic compound (VOC) emissions contribute to the creation of ozone, a main constituent of smog. In the United States of America, VOC regulations established by the Environmental Protection Agency (EPA) and enforced at the state level dictate the maximum concentration of volatile solvents in paints and other products. In Europe, VOC limits are defined by the 2004/42/EC Solvents Directive for Decorative Paints. Water is a volatile component of waterborne paints but it is exempt from VOC regulations as it does not contribute to smog generation. VOC regulations have become more and more stringent to the point that coalescing aids with zero or very low VOC content are now required in order to meet them.

The VOC content of a paint or substance is currently determined in the United States by EPA Method 24 "Determination of Volatile Matter Content, Water Content, Density, Volume Solids, and Weight Solids of Surface Coatings," which incorporates several test methods from the American Society for Testing and Materials (ASTM). Volatile matter content is determined using an oven at 110° C. Any substance, other than water, acetone, and a few other exempt compounds, that evaporates after one hour in this oven is considered a VOC. TEXANOL is classified as a 100% VOC by this test. VOC content is expressed as grams VOC/liter of formulation. In the case of a pure, totally volatile substance, its VOC content equals its density at 25° C. Texanol is 100% volatile in the test and has a VOC content of about 948 g/L. For substances that are partially volatile under the test conditions, only the volatile portion is considered VOC.

In the European Union, a substance having a boiling point below 250° C. at 760 mmHg is considered a VOC. New regulations will require normal boiling points above 280° C. for VOC exemption.

US 2012/0258249 and US 2012/0259049 teach the use of various glycol ether esters as zero VOC coalescing aids and clean-up solvents, respectively. Several preparation methods are described in these patent applications. One of these methods is the Fischer esterification reaction, in which a stoichiometric excess of a reactant bearing a hydroxyl group (e.g., an alcohol or glycol ether) and a carboxylic acid are heated in the presence of a catalytic amount of a strong acid (e.g., concentrated sulfuric acid) and an entrainer solvent (i.e., heptane, toluene, etc.) to yield the desired ester. By-product water is removed by azeotropic distillation. An example of this synthesis can be found in "Unitized Experiments in Organic Chemistry" $3^{rd}$ Edition, by Brewster, VanderWerf, and McEwen, pp. 101-105 (1970). Another method of preparation employs the acid chloride (or dichloride) instead of the carboxylic acid as a reactant. In this case, hydrogen chloride gas is given off instead of water during the reaction. The hydrogen chloride is trapped by the addition of a tertiary amine to the reaction mixture or by means of a water scrubber ("Organic Syntheses, Collective Volume 3," p. 142 (1955)). Another method of preparation, as disclosed in RD 1987276098 A, involves the transesterification of an alkyl ester of the desired acid with a glycol ether in the presence of a suitable catalyst such as tetraisopropyl titanate. Still another method of esterification uses the acid anhydride as reactant in combination with the azeotropic removal of water in the presence of an entrainer. This latter method is often aimed at producing diesters; see, e.g., CA 2,356,469.

The aforementioned processes often yield reaction mixtures that have undesirable odors and color. Color often arises from decomposition of one of the reactants. Volatile esters can be purified by distillation. However, those of low volatility are difficult to purify sufficiently to obtain a product that is relatively free of odor and color. A cumbersome activated charcoal treatment can be used to improve the color and odor of a relatively non-volatile product. Distillation for the purpose of removing color and odor would be extremely difficult to carry out on an industrial scale for some glycol ether esters or diesters, such as bis-dipropylene glycol n-butyl ether adipate (DPnB adipate), given their high boiling points, which often exceed 450° C. WO 2010/079018 teaches that colored esterification products are produced when the alcohol reactant is not treated beforehand to remove color-inducing impurities.

Additional processes for the preparation of glycol ether esters are described in the literature. EP 0711747 B1 teaches that sulfuric acid and p-toluene sulfonic acid catalysts produce color issues in the synthesis of glycol ether acetates by direct esterification, i.e., the Fischer reaction. Products are recovered and purified by distillation. CA 2,746,599 discloses a direct esterification process using as reactants carboxylic and dicarboxylic acids, $C_4$-$C_{13}$ alcohols, alkylene glycol monoethers, and polyalkylene glycols monoethers in the presence of a Lewis acid or Bronsted acid catalyst over a broad reaction temperature range (160-270° C.), and requires a minimum alcohol concentration of 30% excess of the stoichiometric amount. That patent teaches that higher temperatures increase the formation of colored by-products.

Aranda et al., in *Catal. Lett.* (2008) 122:20-25, reported the use of various acids as transesterification catalysts for fatty acids, such as palm oil, for the production of biodiesel. Methanesulfonic and sulfuric acid were the best catalysts, while trichloroacetic acid and phosphoric acid performed poorly.

It would be desirable to have an improved process for the preparation of low-VOC glycol ether esters that would allow production of the desired products in high yield without the need for further treatment, such as charcoal treatment, to remove color and undesirable odor.

SUMMARY OF THE INVENTION

The process of the invention is such a process, comprising contacting in a reaction zone a mono- or di-carboxylic acid and/or acid anhydride with a glycol ether in the presence of a catalytic amount of phosphoric acid under reaction conditions sufficient to produce a reaction product mixture comprising a glycol ether ester product and water, wherein the water is at least partially vaporized in the reaction zone and is passed to a separation zone where the water is substantially removed from the process, and wherein the process is operated under conditions of temperature and pressure such that substantially no glycol ether leaves the separation zone, other than as a component of an azeotrope.

Surprisingly, the process can prepare glycol ether ester solvents with low, or near zero, VOC content as determined by US EPA Method 24 or EU 2004/42/EC Solvents Directive, and can produce said solvents with low color levels.

DETAILED DESCRIPTION OF THE INVENTION

The process of the invention employs a carboxylic acid or anhydride, a glycol ether, and a phosphoric acid catalyst.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

For the purposes of the invention, the term "low boiling" refers to materials having boiling points lower than the boiling point of the relevant glycol ether ester.

For the purposes of the invention, the term "reaction system" refers to a reactor or a plurality of reactors. A plurality of reactors, if employed, is preferably connected in series.

The carboxylic acid or anhydride is aliphatic and contains from 2 to 10, preferably 2 to 7, carbon atoms, and at least 1, preferably no more than 2, carboxyl groups that may, alternatively, be present in the form of anhydride groups. Mono- or di-carboxylic acids are preferred. Examples of the acid or anhydride include: levulinic acid, isopentanoic acid, valeric acid, hexanoic acid, octanoic acid, adipic acid, succinic acid, glutaric acid, malonic acid, fumaric acid, maleic acid, cyclohexane dicarboxylic acid, maleic anhydride, azeleic acid, sebacic acid, substituted maleic and fumaric acids such as citraconic, chloromaleic, mesaconic, and substituted succinic acids such as itaconic acid. It is possible to use mixtures of acids, mixtures of anhydrides, or mixtures of each in any combination. It is also possible to use partial anhydrides.

The glycol ether employed is represented by Formula I:

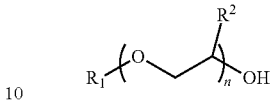

where $R_1$ is a $C_1$-$C_8$ alkyl group, phenyl, or benzyl, $R_2$ is H, methyl or ethyl, and n=1 to 4. In one embodiment of the invention, $R_1$ is a $C_1$-$C_4$ alkyl group. Examples of suitable glycol ethers include ethylene glycol n-butyl ether, ethylene glycol n-hexyl ether, diethylene glycol phenyl ether, tripropylene glycol methyl ether, dipropylene glycol phenyl ether, tripropylene glycol n-butyl ether, dipropylene glycol n-butyl ether, dipropylene glycol n-propyl ether, diethylene glycol n-butyl ether, diethylene glycol n-hexyl ether, butylene glycol ethyl ether, butylene glycol propyl ether, butylene glycol hexyl ether, and dibutylene glycol methyl ether. Mixtures of glycol ethers may be employed. In one embodiment of the invention, the molar ratio of glycol ether to carbonyl moiety of carboxylic acid or anhydride is from 1.05 to 1.25 in the system over the course of the reaction.

Phosphoric acid is widely commercially available. The phosphoric acid is employed in a catalytic amount. Advantageously, the amount of phosphoric acid is from about 2 to about 10, preferably from 4 to 8, mole percent, based on the moles of carboxylic acid or anhydride. In one embodiment of the invention, the phosphoric acid is employed in the form of an aqueous solution. The phosphoric acid content of the solution is not particularly critical. In one embodiment of the invention, the phosphoric acid is supplied as an aqueous solution of 85% phosphoric acid.

The invention is a process for preparing carboxylic esters by reacting a carboxylic acid or a carboxylic anhydride or a mixture thereof with a glycol ether in a reaction system comprising at least one reactor, with water being distilled off in a separation zone as a glycol ether-water azeotrope with the vapor coming out of the reaction liquid, the vapor then being at least partly condensed, and at least part of the condensate being returned as reflux to the separation zone and/or reaction system. The process is an esterification process that operates under a set of reaction and process conditions that allow the glycol ether ester products to be produced in a relatively short reaction time in a direct esterification process (i.e., Fischer reaction), in high yield, and relatively free of color and undesirable odors. In one embodiment of the invention, the separation zone comprises a distillation column and the distillation column is operated using a process control scheme that includes controlling the temperature at the top of the column.

In one embodiment of the invention, the process is conducted in a reactor equipped with a distillation column. The column may be separate from the reactor or, preferably, is a column mounted on the reactor. The column advantageously is equipped with or connected to a condenser. As the reactive distillation proceeds, by-product water of reaction forms an azeotrope with the glycol ether. The reactor and column advantageously are operated under conditions of temperature, pressure and reflux ratio such that substantially only the azeotrope exits the column overhead. In this manner, essentially no glycol ether reactant leaves the column, other than as a component of the azeotrope. Water vapor is removed from the reactor as a component of the azeotrope.

The vapor is condensed, and part of the condensate is returned as reflux to the column. The amount of condensate returned is determined by the temperature of the condensate and determined by the energy balance requirements of the system. In one embodiment of the invention, the operation of the column is controlled by observing the temperature at the top of the column. The temperature can also be observed at other points in the column, as is known to those skilled in the art. In one embodiment of the invention, the maximum temperature in the separation zone is less than the boiling point of the pure glycol ether. In one embodiment of the invention, the process is conducted in the substantial absence of oxygen.

In one embodiment of the invention, the temperature and pressure conditions in the system are such that the temperature of the reaction mixture is lower than its boiling point. The process advantageously employs a reaction temperature of from 170 to 210° C., i.e., the average temperature of the liquid in the reaction zone advantageously is in this range. The reaction pressure is, as is known to those skilled in the art, related to the reaction temperature and the extent of completion of the reaction. In various embodiments of the invention, the reaction pressure can be from 10 to 2500 mmHg absolute (1.3 kPa to 333 kPa), or from 50 mmHg (6.7 kPa) to 760 mmmHg absolute (101 kPa).

In one embodiment of the invention, as the reaction proceeds, by-product water is removed via the column, and the desired product concentrates in the reactor. The extent of completion of the reaction can be observed by tracking the amount of water produced, or by other methods known to those skilled in the art.

The starting materials and the catalyst can be introduced into the reactor in any suitable order, e.g., either simultaneously or otherwise, when the process is carried out batchwise. The catalyst can be introduced in pure form or as a solution, preferably as a solution in water or one of the starting materials, at any suitable point in the process.

In the case of a continuous process, streams of the starting materials and of the catalyst are fed into the reactor or, when a reactor cascade is used, preferably into the first reactor of the cascade. The residence time in the reactor or the individual reactors is determined by the volume of the reactors and the flow rate of the starting materials.

The reaction can be conducted in any suitable equipment, using any suitable materials of construction, as is well known to those skilled in the art.

In one embodiment of the invention, at the end of the reaction, the reaction product mixture advantageously is neutralized, the resulting salt or salts are extracted, and the product is recovered. In one embodiment of the invention, at the end of the reaction, an alkaline material is contacted with the reaction product mixture under conditions sufficient to neutralize the major portion of any acids therein, thereby forming a neutralized product mixture comprising a glycol ether ester product and at least one salt. For example, the catalyst and residual carboxylic acid can be neutralized using the alkaline material. In one embodiment of the invention, all of the catalyst is neutralized, i.e., at least the first hydrogen atom of the phosphoric acid catalyst is replaced with some portion of a molecule of the alkaline material, and at least a portion of any residual unreacted carboxylic acid is neutralized. In one embodiment of the invention, at the end of the reaction, the reaction product mixture is at least partially cooled prior to and/or during neutralization.

The alkaline material advantageously is employed in an amount that is sufficient to neutralize the acid catalyst. The amount of alkaline material required can readily be determined by those skilled in the art. Examples of alkaline materials include: glycol ether alkoxides; alkali metal and alkaline earth metal compounds, such as NaOH, MgOH, CaOH, KOH, sodium carbonate and sodium bicarbonate; alkaline solids, such as alkaline alumina and alkaline ion exchange resins; and the like. Soluble alkaline materials may be added as a solution, e.g., as an aqueous solution. Mixtures of alkaline materials can be employed. It is believed, without being bound by any theory, that neutralizing the reaction product mixture before separating residual glycol ether aids in the production of a low color product.

In one embodiment of the invention, the process further comprises extracting one or more salts formed during neutralization. This advantageously is accomplished by allowing the salts to migrate to the aqueous phase of a multiphase mixture that forms when the alkaline material is introduced to the reaction product mixture. The extraction step is conducted for the purpose of separating the salts, which are produced by the neutralization step, from the mixture. The extraction step may aid in color removal from the product. The extraction optionally can involve adding additional solvent, e.g., water, and/or an extraction aid, to the reaction product mixture and/or the neutralized crude product mixture to facilitate extraction of the salts.

The optional extraction aid is a water-soluble material that serves at least one of the following functions: to break potential emulsions; to improve the separation of the aqueous and organic layers; and/or to improve the extraction of the salts into the aqueous phase. The amount of extraction aid that may be employed can readily be determined by those skilled in the art. In one embodiment of the invention, from 0.1 to 10 weight parts of extraction aid are employed per 100 weight parts of the neutralized product mixture. Examples of suitable extraction aids include water-miscible organic species: such as ketones, such as acetone; and alkanols, such as isopropanol and n-propanol. Mixtures of extraction aids can be employed.

The neutralization and extraction may be performed concurrently or sequentially. If performed sequentially by first conducting the neutralization, and then conducting the extraction, as will be recognized by those skilled in the art, it is likely that some extraction will occur during the neutralization. Thus, regardless of whether an extraction aid is added at toward the start of neutralization of after neutralization is complete, neutralization and extraction are occurring simultaneously, to some extent. For the purposes of the invention, the term "simultaneously," when used in connection with the neutralization reaction and extraction of the reaction product, means that at some point the extraction and the neutralization reaction are both occurring at the same time. As will be recognized by those skilled in the art, at the start of the neutralization reaction there will be very little to no extraction occurring. The rate of extraction will increase as more salt becomes available in the neutralized crude product mixture. Thus, as a practical matter, once a salt forms as a result of neutralization, it is possible for some extraction to occur, as is well known to those skilled in the art. In one embodiment of the invention, the process further comprises a neutralization/extraction step wherein the reaction product mixture is contacted with an alkaline material to produce a neutralized product mixture comprising an organic phase and an aqueous phase, the neutralized product mixture comprising a glycol ether ester product and at least one salt, and wherein the contacting is conducted under conditions sufficient to extract the at least one salt into the aqueous phase.

In various embodiments of the invention, the process comprises adding water, and optionally an extraction aid, to the reaction product mixture and/or the neutralized product mixture to extract the salt(s) formed during neutralization, and allowing phase separation, then recovering the organic phase comprising the neutralized product. Recovery of the organic phase can be accomplished by separating either the organic phase or the aqueous phase from the other phase. For example, the organic phase can be decanted from the aqueous phase to obtain a crude product. The organic phase is retained for further processing. The salt-containing aqueous phase can be discarded or can be processed to recover its contents according to methods well known to those skilled in the art.

The product-containing organic phase is processed to recover the product using methods known to those skilled in the art. For example, water, glycol ether, and low boiling organics can be removed from the organic phase by any suitable means including, for example, distillation and/or vacuum stripping with an inert gas, such as nitrogen to produce a purified product. Advantageously, the maximum stripping temperature preferably is below 170° C. in order to minimize the formation of color bodies. In one embodiment of the invention, the salt-free crude product is vacuum stripped then distilled. The conditions employed can be readily determined by those skilled in the art, depending on the product being produced.

In one embodiment of the invention, the organic phase is stripped to remove water and low boiling organics to produce a low VOC, low color glycol ether ester product without requiring a final distillation step where the product is recovered overhead. This is surprising, as distillation to recover the product overhead would normally be expected to be required in order to obtain such a low color product. Thus, in one embodiment of the invention, the process is conducted such that the product is recovered as a bottoms product.

In one embodiment of the invention, an additional filtering step is employed after stripping to remove solid salts from the liquid phase. This filtering step can be performed as desired at various points in the process, as is known to those skilled in the art. It is also possible, in some cases, as is known to those skilled in the art, to avoid the formation of solid salts, and in such a case no filtering is needed.

In a particularly preferred embodiment of the invention, the process is a process for the production of DPnB adipate. This embodiment includes following steps:

(1) Reacting dipropylene glycol n-butyl ether (DPnB) and adipic acid in the presence of a catalytic amount of phosphoric acid, with removal of by-product water by azeotropic distillation. In order to minimize color formation during the reaction step, the temperature and pressure conditions in the system are such that the temperature of the reaction mixture is lower than its boiling point.

(2) Cooling the reaction product mixture to 80° C. or lower.

(3) Neutralizing the phosphoric acid catalyst by adding aqueous sodium hydroxide or another suitable base to the reaction product mixture to form a neutralized product mixture comprising salts.

(4) Extracting the salts, such as sodium phosphate when using NaOH or another sodium-containing base to neutralize, from the neutralized reaction mixture with a combination of water and isopropanol, thereby removing the salts, including salts of organic by-products. In one embodiment of the invention, the amount of isopropanol employed is about 1% by weight based on the reaction mass at the end of the reaction.

(5) Allowing the organic phase and aqueous phase formed in steps (3) and/or (4) to separate, and recovering the organic phase.

(6) Purifying the organic phase. This involves removing residual water, DPnB and lighter, i.e., lower boiling than the product ester, organics under vacuum using heating, with inert gas stripping, e.g., with nitrogen. The maximum stripping temperature preferably is below 170° C. in order to minimize the formation of color bodies.

(7) Optionally, filtering residual solids from the desired product.

In one embodiment of the invention, following the reaction wherein the glycol ether is dipropylene glycol n-butyl ether (DPnB), and the carboxylic acid is adipic acid, the process further comprises:

a) contacting the reaction product mixture with NaOH, and optionally an extraction aid, preferably isopropanol, to produce a neutralized product mixture comprising an organic phase and an aqueous phase, the neutralized product mixture comprising DPnB adipate product and at least one salt, and wherein the contacting is conducted under conditions sufficient to extract the at least one salt into the aqueous phase, (b) allowing the organic phase and the aqueous phase to separate, then recovering the organic phase, (c) purifying the organic phase by removing residual water, DPnB and lighter, i.e., lower boiling than the product DPnB adipate, organics under vacuum using heating, optionally with inert gas stripping, (d) optionally, filtering residual solids from the product.

Some aspects of the specific conditions and step sequence are important to obtain colorless material with good yield from the feed material. For example, deviation from the temperature/pressure condition mentioned in step (1) leads to excessive loss of DPnB and formation of color in the product. Doing step (5) before the neutralization may also lead to color formation in the material. In the absence of the extraction step (4), the final product may contain additional intermediate by-products, particularly, monoesters of adipic acid and olefin-containing compounds. This can lead to additional volatility of the produced product, i.e., VOC content, and diminish its efficacy as a low VOC coalescing aid.

The glycol ether ester product of the process is described by Formulas II and III.

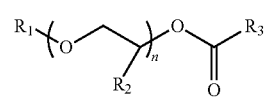

Formula II where $R_1$ is a $C_1$-$C_8$ alkyl group, phenyl or benzyl, $R_2$ is either hydrogen, methyl or ethyl, $R_3$ is a $C_4$-$C_7$ alkyl group or a 4-oxopentanoyl group, and n=1 to 4. Some examples of glycol ether esters described by this formula include ethylene glycol n-butyl ether isopentanoate, diethylene glycol phenyl ether valerate, tripropylene glycol methyl ether octanoate, dipropylene glycol n-butyl ether hexanoate, dipropylene glycol phenyl ether levulinate, and tripropylene glycol n-butyl ether isopentanoate.

Formula III

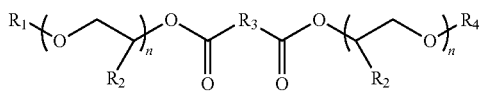

where $R_1$ and $R_4$ independently are $C_1$-$C_8$ alkyl groups, phenyl or benzyl, $R_2$ independently is either hydrogen, methyl or ethyl, n=1 to 4, and $R_3$ is a carbon chain containing 0-5 carbon atoms and may contain a double bond. Preferably, $R_1$ and $R_4$ independently are $C_1$-$C_8$ alkyl groups. Some examples of bis-glycol ether esters described by this formula include DPnB Adipate, bis-dipropylene glycol n-propyl ether adipate, bis-diethylene glycol n-butyl ether malonate, bis-diethylene glycol n-butyl ether succinate, and bis-dipropylene glycol n-butyl ether maleate.

In one embodiment of the invention, the purified and/or final product contains less than 1% of volatile organic compounds as defined by EPA Method 24. In one embodiment of the invention, the color of the purified and/or final product is less than 25 APHA, as measured ASTM D1209. In one embodiment of the invention, the purified and/or final product has a boiling point above 250° C. at 760 mmHg, measured as defined in the 2004/42/EC Solvents Directive for Decorative Paints.

SPECIFIC EMBODIMENTS OF THE INVENTION

The following example is given to illustrate the invention and should not be construed as limiting its scope. All pressures are absolute, not gauge, unless otherwise indicated.

Example 1: Manufacture of DPnB Adipate

A 10-gallon, 316 stainless steel reactor, rated for 750 psig (5.27 Mpa), equipped with a variable speed agitator/impeller, a nitrogen sparger, a cartridge filter, and a multiple use pipeline header is used. The reactor body is jacketed and the reactor head is traced to provide means for heating and cooling with SYLTHERM 800 brand heat transfer fluid, which is available from The Dow Chemical Company. The reactor is connected to a 5-foot×4-inch stainless steel, jacketed column packed with 5 feet of Goodloe brand structured packing. The column is equipped with an overhead 316 stainless steel, 2-pass heat exchanger with a total surface area of 25 square feet as a condenser, which is connected to a receiving vessel and to a vacuum system. The head of the reactor is operated at reduced temperature relative to the reactor jacket to minimize degradation reactions. For the reaction, the reactor head tracing and the column jacket are operated at the same temperature of 95° C. This is selected to minimize the loss of reactants in the overheads. The reactor and peripheral equipment are operated with a process control unit.

The reaction step is performed as follows: The initial materials are well mixed at 120 rpm using the built in agitator/impeller. The initial pressure in the reactor is ~550 mmHg (73 kPa). The reactor is heated by heating oil up to 190° C. in 2.5 hrs, and is maintained at that temperature for ~6 hours. After two hours of heating and reaching 177° C., the pressure is reduced to ~60 mmHg (8 kPa) for the next two hours of operation. During the pressure decrease, special attention is paid to the column overhead temperature, which is maintained at or below the boiling point of the DPnB/water azeotrope. This ensures that the DPnB concentration in the vapor does not exceed the DPnB concentration of the water/DPnB azeotrope. Vapor from the column is condensed at 5° C. in the overhead condenser. Part of the condensed material is returned in the column as reflux. The progress and rate of the esterification reaction between DPnB and adipic acid is monitored by the amount of recovered distillate and by the rate that column overhead distillate is produced. At the end of the reaction step, when the recovered overhead distillate mass approaches the expected target and the distillate flow rate approaches zero, the reactor pressure is increased to 760 mmHg (101 kPa) and the reactor content is cooled to 80° C. By analysis, the reactor contains 91.64% wt DPnB adipate, 6.71% wt DPnB, 2.90% wt monoester of DPnB and adipic acid and 0.014% wt of water (the analysis is performed only for organic components and water, using gas chromatography (GC) and Karl Fischer titration, respectively). The GC analysis is performed using a Hewlett-Packard 6890 Gas Chromatograph equipped with flame ionization and thermal conductivity detectors, and a Hewlett-Packard 7673 auto-injector with a 100-sample tray. The instrument is linked to a Hewlett-Packard ChemStation comprising an IBM computer with HP62070AA software. The DPnB, the adipic acid, and the DPnB Adipate are analyzed in a 30 m×0.32 mm ID×1.5μ film Restek RTX200 capillary column using a constant helium column pressure of 15 psig (205 kPa). The dipropylene glycol n-butyl ether adipate monoester is analyzed in a 30 m×0.25 mm ID×0.25μ film Zebron ZB-1 capillary column using a constant helium flow of 1.1 mL/minute. The injector and detector temperatures are set at 300° C. and the oven temperature is programmed from 100° C. to 290° C.

At this point, 0.386 kg sodium hydroxide is added to the mixture in the reactor, based upon titration and the expected neutralization requirement, as a 50% solution (0.772 kg). The materials are mixed at 60 rpm using the built in agitator/impeller. Calculation of the amount of NaOH needed for the neutralization of the catalyst advantageously is accomplished using the formula:

$$NaOH_m = (0.125 R_m \times MAD_x) + (0.8164 \times H_3PO_{4_m})$$

where
$NaOH_m$=Mass of sodium hydroxide (kg)
$R_m$=Current reaction mass (kg)
$MAD_x$=Mono–adipate mass fraction
$H_3P_{4_m}$=Mass of phosphoric acid loaded 100% basis (kg)
Analysis of the neutralized reaction mixture by GC shows 0.21-0.43% remaining unneutralized monoester.

A mixture of 3.677 kg water and 0.28 kg isopropanol (IPA) is added to the reactor to extract most of the salt. IPA is added at ~1/100th of the expected reaction mass remaining after completion of the reaction. The materials are mixed at 60 rpm using the built in agitator/impeller.

The agitator/impeller is slowed to 15 rpm, the phases are allowed to separate, and 5.53 kg of the aqueous-salt layer is drained from the reactor, of which the last ~0.08 kg is brown in color. The first aqueous 5.45 kg is colorless. 1.02 kg of reaction mixture trapped in process lines is finally drained and is also colorless.

The reactor pressure is reduced to 25 mmHg absolute (3 kPa) and the reactor is heated up to 170° C., and nitrogen is then introduced to strip any remaining traces of unreacted DPnB. The reactor effluent is condensed in the overhead condenser and accumulated without refluxing in the column. The reactor pressure is raised to 760 mmHg and its temperature is lowered to 25° C. The reactor is drained and the drained material has a sample composition by GC of 104% wt DPnB adipate, 0.05% wt DPnB and 0.17% wt water. The >100% value for DPnB adipate falls within the ±5% error for the analysis of this compound when it is present as the main component.

The reactor content is filtered using the cartridge filter to remove the salt and the filtered material is analyzed by GC. The filtered sample composition is 98% wt DPnB adipate, 1.2% wt DPnB and 0.25% wt water. The material color is 10.3 APHA and the VOC % is 0.5.

Comparative Experiment 2: Manufacture of DPnB Adipate—Neutralization after Stripping (not an Embodiment of the Invention)

The following materials are charged to the reactor system of Example 1, in kg: 7.5 adipic acid, 22.9 DOWANOL™ DPnB brand glycol ether (available from The Dow Chemical Company), 0.473 85% phosphoric acid (aq.) and 0.25 deionized water. The mixture has approximately the same composition as the starting mixture of Example 1, and has a 2.25 molar ratio of DOWANOL™ DPnB to adipic acid and 8% mol of phosphoric acid based upon adipic acid. The mixture is heated to 190° C. The reactor pressure is decreased from 800 mmHg to 120 mmHg (107 kPa to 16 kPa) during the heating period. The reactor is kept at these conditions for 6 hrs. The esterification reaction progress manifests itself by the production of water. The vapor from the reactor is condensed in the column condenser at 5° C. Part of the condensed material is returned in the column as the reflux flow. The overhead temperature of the column varies in the range of 65-80° C., which is 10-25° C. higher than the temperature of DPnB/water azeotrope at this pressure. A sample of reactor content taken at the end of this period indicates that material in the reactor contains 91% wt DPnB adipate, 13% wt DPnB and 3% wt monoester. All adipic acid is consumed by the reaction. The color of a 3.3 kg sample is 27 APHA, which exceeds the color target maximum of 25 APHA. The reactor pressure is gradually decreased to 10 mmHg (1.3 kPa) in order to remove the remaining DPnB from the reactor. The overhead temperature of the column gradually increases to 122° C., which is significantly higher than the boiling point of the DPNB/water azeotrope and is more consistent with the boiling point of pure DPnB at this pressure.

A sample of reactor content is taken after 3 hrs at these conditions. The composition of the sample is 99.5% of DPnB adipate, 0.4% wt of DPnB and 3.6% wt of monoester. The sample has a dark brown color, significantly exceeding 100 APHA. As in Example 1, the material is cooled to 80° C., and is treated with 0.29 kg of sodium hydroxide and 12 kg of water. The quantity of sodium hydroxide is consistent with the remaining amount of phosphoric acid present after the large 3.3 kg sample is removed with a 2 mole ratio of sodium hydroxide to phosphoric acid. A sample is taken after neutralization. The composition of the sample is 97.9% of DPnB adipate, 0.5% wt of DPnB and 3.5% wt of monoester. These steps did not significantly improve the color of the material, which is significantly higher than 100 APHA.

These two examples illustrate the importance of the procedures described in the invention. The material in the reactor is heated to the same temperature (190° C.); nevertheless, in Example 1 the final product has very little color, while in the Comparative Experiment 2 the final product has a dark brown color. In Ex. 1, the process involves neutralizing before stripping, while C.E. 2 does not.

What is claimed is:

1. A process for the preparation of a glycol ether ester, the process comprising contacting in a reaction zone a mono- or di-carboxylic acid and/or acid anhydride with a glycol ether of the following formula:

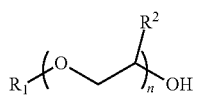

wherein $R_1$ is a $C_1$-$C_8$ alkyl group, phenyl, or benzyl, $R_2$ is H, methyl or ethyl, and n=1 or 4, in the presence of a catalytic amount of phosphoric acid under reaction conditions sufficient to produce a reaction product mixture comprising a glycol ether ester product and water, wherein the water is at least partially vaporized in the reaction zone and is passed to a separation zone where the water is substantially removed from the process, wherein the process is operated under conditions of temperature and pressure such that essentially no glycol ether leaves the separation zone, other than as a component of an azeotrope, wherein the temperature at the top of the separation zone is at most the boiling point of the azeotrope, and wherein the azeotrope is formed by water and the glycol ether.

2. The process of claim 1 wherein the maximum temperature in the separation zone is less than the boiling point of the pure glycol ether.

3. The process of claim 1 further comprising a neutralization/extraction step wherein the reaction product mixture is contacted with an alkaline material to produce a neutralized product mixture comprising an organic phase and an aqueous phase, the neutralized product mixture comprising a glycol ether ester product and at least one salt, and wherein the contacting is conducted under conditions sufficient to extract the at least one salt into the aqueous phase.

4. The process of claim 3 further comprising allowing phase separation, then recovering the neutralized product.

5. The process of claim 4 further comprising heating the neutralized product at subatmospheric pressure to remove water and low boiling organics to produce a purified product.

6. The process of claim 5 further comprising filtering the purified product to produce a final product comprising the glycol ether ester product.

7. The process of claim 1 wherein the molar ratio of glycol ether to carbonyl moiety of carboxylic acid or anhydride is from 1.05 to 1.25 over the course of the reaction.

8. The process of claim 1 wherein the purified and/or final product has a color of less than 25 APHA.

9. The process of claim 1 wherein the VOC content of the purified and/or final product is less than 1 weight percent as determined by EPA Method 24.

10. The process of claim 1 wherein the product has a boiling point above 250° C. at 760 mmHg, measured as defined in the 2004/42/EC Solvents Directive for Decorative Paints.

11. The process of claim 1 wherein the glycol ether comprises DPnB and the ester comprises DPnB adipate.

12. The process of claim 1 wherein the separation zone comprises a distillation column and the distillation column is operated using a process control scheme that includes controlling the temperature at the top of the column.

13. The process of claim 1 wherein the glycol ether is dipropylene glycol n-butyl ether (DPnB), and the carboxylic acid is adipic acid, the process further comprising:
 (a) contacting the reaction product mixture with NaOH, and optionally an extraction aid, preferably isopropanol, to produce a neutralized product mixture comprising an organic phase and an aqueous phase, the neutralized product mixture comprising DPnB adipate product and at least one salt, and wherein the contacting is conducted under conditions sufficient to extract the at least one salt into the aqueous phase,
 (b) allowing the organic phase and the aqueous phase to separate, then recovering the organic phase,
 (c) purifying the organic phase by removing residual water, DPnB and organics having a lower boiling point than the glycol ether ester product under vacuum using heating, optionally with inert gas stripping,
 (d) optionally, filtering residual solids from the product.

* * * * *